United States Patent [19]

Stein

[11] 4,180,574
[45] Dec. 25, 1979

[54] CERTAIN OVICIDAL PIPERAZINES

[75] Inventor: Robert G. Stein, Kenosha, Wis.

[73] Assignee: Abbott Laboratories, North Chicago, Ill.

[21] Appl. No.: 973,355

[22] Filed: Dec. 26, 1978

[51] Int. Cl.² ............................................. A01N 9/22
[52] U.S. Cl. .................................................. 424/250
[58] Field of Search ........................ 424/250; 544/392

[56] References Cited

U.S. PATENT DOCUMENTS 2,993,899  7/1961  Dawson .............................. 544/392

Primary Examiner—V. D. Turner
Attorney, Agent, or Firm—Paul D. Burgauer; Robert L. Niblack

[57] ABSTRACT

It has been found that compounds of the structure

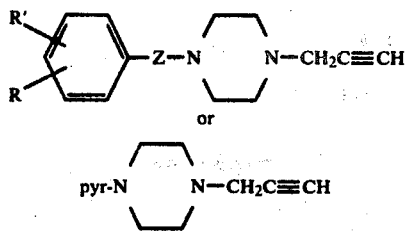

wherein "pyr" stands for 2-, 3-, or 4-pyridyl; Z is CO or $(CH_2)_n$; n is 0, 1 or 2; R is hydrogen, halogen, loweralkyl, loweralkyloxy, nitro, or hydroxymethyl; and R' is hydrogen or halogen are excellent insect ovicides.

9 Claims, No Drawings

CERTAIN OVICIDAL PIPERAZINES

DETAILED DESCRIPTION OF THE INVENTION

Some compounds of the nature of N-propargyl-N'piperazine have been known to be useful antihistamines or anticholinergics. It has now been found that particular compounds of this series have unique ovicidal activity.

The present invention is directed to the process of preventing maturation of eggs of crop-damaging insects, consisting essentially in applying to the habitat of said eggs an ovicidal amount of a compound of the formula

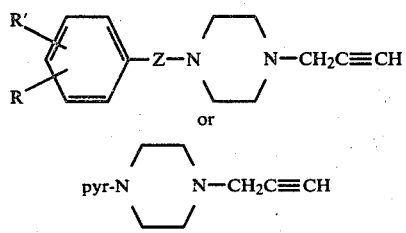

wherein "pyr" stands for 2-, 3-, or 4-pyridyl; Z is CO or $(CH_2)_n$; n is 0, 1 or 2; R is hydrogen, halogen, loweralkyl, loweralkyloxy, nitro, or hydroxymethyl; and R' is hydrogen or halogen and salts thereof, together with an agriculturally acceptable diluent. The above reference to "loweralkyl" is meant to include those alkyl groups that contain 1–4 carbon atoms. Some of the compounds used in the present invention are known from U.S. Pat. No. 2,993,899 where it is disclosed that they are useful as anticholinergics or antihistamines.

Among the agriculturally acceptable diluents, water is the most convenient one, although water is seldom used alone since detergents, wetting agents and the like are often necessary or desirable to provide a more homogeneous solution or dispersion of the active material. Solid diluents are often more suitable than liquids, as storing, shipping and packaging is easier than in liquid products.

The compounds of the current invention may be applied in the form of emulsifiable concentrates, powders, granules or dusts. An agronomically acceptable carrier for the purposes of this invention includes any substance which can be used to dissolve, disperse or diffuse the above novel compounds, without impairing the effectiveness of the active ingredient, and which is not deleterious to the soil or the plant in any chemical or physical manner. Particularly favored compositions are those wherein the active ingredient is present in a range from 1–20% by weight and the mixture of active compound and the diluent form a water-emulsifyable concentrate or it is a wettable powder. Solid diluents of this nature are well known in the agricultural formulation art. They include clay, diatomaceous earth, bentonite, etc.

In formulating the composition of this invention, other components may be included to aid in the adsorption or absorption of the active ingredients by the plant. Components such as wetting agents, solubilizers, emulsifiers, humidifants, surfactants and other adjuvants useful for this purpose may be incorporated in the formulations.

The above compounds are preferably compounded with inert diluents to a liquid or solid composition containing between 10,000 and 200,000 ppm, particularly compositions containing 25,000 to 50,000 ppm. Such stock mixes are easily packaged and stable and can be diluted by the consumer to the necessary concentrations of between 500 to 2,500 ppm.

The compounds of the present invention can be made by three different routes. Availability or convenience of starting materials will indicate to the skilled, which of these three routes are preferred in each instance. The three methods are:

A. An appropriately substituted benzoyl chloride is condensed with N-propynylpiperazine in the presence of an acid acceptor. This method is preferred where Z is a carbonyl group.

B. An appropriately substituted benzamide, aniline or phenylalkylamine is refluxed with bis(2-haloethyl)propynylamine. This method does not always produce the best yields.

C. N'-substituted piperazine carrying the entire desired phenyl, benzyl, benzoyl, phenethyl or pyridyl moiety is reacted with propynyl halide. This is the method of choice when Z is alkylene or N' carries pyridyl.

In order to illustrate specific embodiments of the present invention, reference is made to the following examples, which, however, are not intended to limit the scope of this invention. In all of these examples, the microanalyses of the produced compounds were found to be in excellent agreement with the expected calculated values for these products.

EXAMPLE 1

A solution of 5.6 g. of benzoyl chloride was added to a stirred solution of 1.96 g. of N-propynyl piperazine, 4.04 g. of triethylamine and 100 ml. of chloroform. The mixture was stirred 4 hours, filtered and the filtrate washed in sequence with 100 ml. of water, 100 ml. of 5% aqueous potassium carbonate and 100 ml. of water. The chloroform solution was then evaporated in vacuo to produce a white solid. Crystallization from cyclohexane produced the expected white crystals of N'-benzoyl-N-propynyl piperazine, m.p. 94°–5° C.

EXAMPLE 2

A mixture of 6.44 g. of 4-chlorobenzyl chloride, 4.97 g. of N-propynyl piperazine, 8.48 g. of sodium carbonate and 50 ml. of ethanol was refluxed for 18 hours. The mixture was then filtered and the filtrate evaporated in vacuo. The residual oil was dissolved in chloroform which solution was washed with water and then dried over magnesium sulfate. The mixture was then filtered and the filtrate was evaporated under vacuum and subsequently distilled to give a yellow oil of the expected N'-(4-chlorobenzyl)-N-propynyl piperazine, b.p. 162°–5° C./1.5 mm, which produces a single spot of T.L.C. and the expected NMR and IR spectra.

EXAMPLE 3

A mixture of 6.5 g. of N-bis(2-chloroethyl)propynylamine hydrochloride, 19.4 g. of 3,4-dichloroaniline and 60 ml. of isopropanol was refluxed for 18 hours. The mixture was then evaporated and water was added to the residue. This solution was made strongly alkaline by adding 40% aqueous potassium hydroxide and extracted several times with ether. The combined ether extracts were evaporated to produce an oil. This oil was passed through Florisil column using ethyl acetate as the eluate. The first material eluted from the column was found to be the desired N'-(3,4-dichlorophenyl)-N-propynyl piperazine. The NMR and IR spectra and microanalysis confirm the structure of this product.

EXAMPLE 4

Propynylbromide (11.9 g.) was added to the sodium salt of N-(2-pyridyl)piperazine prepared from 16.3 g. of N-(2-pyridyl)piperazine and 4.8 g. of sodium hydride/50% mineral oil dispersion in 50 ml. of dry dimethylformamide. The mixture was stirred at 50° C. for 3 hours and then carefully poured into 3 volumes of cold water. This mixture was extracted with several portions of either and the combined ether extracts were washed twice with 10% aqueous hydrochloric acid. The acidic extract was made strongly alkaline by adding 40% aqueous sodium hydroxide under cooling. The mixture was then extracted several times with ether and the combined extracts were dried over magnesium sulfate. The latter was then removed by filtration, and the filtrate was evaporated to produce a brown oil. Distillation under reduced pressure gave N'-(2-pyridyl)-N-(2-propynyl)piperazine, b.p. 153°-4° C./3.5 mm, as a yellow oil which showed the expected NMR and IR spectra.

EXAMPLES 5-9

In the manner described in Example 4, the following N'-substituted N-propynyl piperazines were made:

| Example No. | N'-Substituent | Phys. Properties |
|---|---|---|
| 5 | phenyl | 117°-9° C./0.7 mm. |
| 6 | benzyl | 123°-7° C./1 mm. |
| 7 | 2-methoxyphenyl | oil |
| 8 | 4-Me-3-Cl-phenyl | 170°-5° C./3 mm. |
| 9 | 4-HOCH$_2$-3-Br-phenyl | m.p. 103°-4° C. (pentane) |

EXAMPLES 10-14

By the method of Examples 1 and 3, the following N'-substituted N-propynylpiperazines were made:

| Example No. | N'-Substituent | Phys. Prop. | Ref. |
|---|---|---|---|
| 10 | 3-chlorophenyl | oil | Ex. 3 |
| 11 | 4-chlorophenyl | oil | Ex. 3 |
| 12 | phenethyl | oil | Ex. 1 |
| 13 | benzoyl | m.p. 94°-5° C. (cyclohexane) | Ex. 1 |
| 14 | 4-nitrophenyl | m.p. 107°-8° C. (isopropanol) | Ex. 1 |

Fresh strips are taken from an appropriate cage of young adult cabbage loopers. This strip is disinfected for 10 minutes in a 10% formaldehyde solution. This step is necessary to surface sterilize the eggs to prevent extraneous mortality to newly emerged larvae from viruses and other pathogens. After treatment in the formaldehyde solution, egg strips are rinsed in running tap water for thirty minutes and then allowed to air dry. Following drying, the egg strips are cut into 1 inch squares. One square containing no less than 10 eggs is used for each test compound. Initial tests are carried out at 500 ppm made from a stock solution of 50,000 ppm in a DMF/isopropanol 1:3 (vol.) mixture containing 4% of a commercial wetting agent; the diluent is a 70% aqueous acetone mixture.

An egg patch is placed into a Buchner funnel, attached to a vacuum source. Ten ml. aliquots of the appropriate compound are poured directly onto the patch. The chemical is immediately removed by suction. The egg patch is allowed to air dry and the number of eggs per patch is recorded. The treated eggs are then placed in a disposable petri dish (100×20 mm.) containing 30 ml. of normal looper rearing media (casein, alfalfa meal, wheat germ diet). A disc of filter paper 11 cm. in diameter is placed over the dish. The plastic lid is then pressed over the filter paper to seal the dish, which are then incubated at 30±1 degrees C. for six days.

To evaluate activity, the number of larvae emerging from each egg patch are counted. The resulting count is compared to the number of eggs contained in the patch and percent emergence is then calculated. The compounds were treated at various concentrations, starting with 500 ppm.

The results are shown under heading A of Table II, using the following ratings: 0-20% emergence=3; 20-50% emergence=2; 50-75% emergence=1 and 75% emergence=0.

In the same fashion as above, some of the above compounds are also tested against eggs of the *Heliothis verescens* (tobacco bud worm) at 500 ppm. The results are shown in column B, using the same rating scale. In this test, the larvae are counted after three days instead of the above 6-day span.

Table II

| Compound of | A: Test Concentrations | | | | Test B |
|---|---|---|---|---|---|
| Example No. | 500 | 250 | 125 | 63 | 500 ppm |
| 2 | 3 | 3 | 3 | 2 | 2 |
| 4 | 3 | 3 | 2 | 0 | 3 |
| 5 | 3 | 3 | 1 | 2 | 2 |
| 6 | 3 | 3 | 2 | 1 | 2 |
| 9 | 1 | NT | NT | NT | NT |
| 10 | 3 | 3 | 2 | 1 | 3 |
| 11 | 3 | 3 | 3 | 3 | 2 |
| 12 | 3 | 2 | 2 | 2 | NT |
| 13 | 2 | 2 | 1 | 1 | NT |

NT = not tested

As seen from the above results, the compounds used for the current procedure are highly effective in preventing larvae development. This ovicidal activity is of great commercial interest because of the damage that can be caused by the hatching insects. While the above tests are directed to specific eggs only, it will be understood that these compounds have ovicidal effect over a much wider variety of insect eggs; however, the above identified species are among the most difficult ones to combat and it is generally accepted that ovicides used successfully against cabbage loopers and corn-ear worms are effective also in combating the hatching of eggs of other crop-damaging insects, i.e., the entire heliothis family.

As described above, the current compounds are commonly applied in diluents, preferably at a concentration of 100-1000 ppm. Wettable powders which may optionally contain other ingredients useful in combating agricultural pests (fungicides, insecticides, etc.) are ordinarily prepared by use of 0.01-0.1% by weight of a wetting agent such as an alkyl sulfate, an aralkyl sulfonate, a sulfosuccinate, a polyethylene glycol ether or the like. Dusting powders are made with the current ovicides and a finely divided, inert diluent. In this instance, the above range of 0.01–0.1% by weight of the new ovicide is also preferred and again, other agricultural control agents may be included in such a compound.

The above examples are directed to the use of the compounds per se with the depicted structure. Their simple salts can be used in similar fashion and frequently, their preparation is easier than that of the free compound as it allows the use of the appropriate acid in the isolation or purification steps. Among the most common acids that frequently add to the above bases are the hydrochloric, sulfuric, acetic, oxalic, maleic or succinic acids. Other organic acids can also be used but they are less economical than the above.

I claim:

1. A method of combating the hatching of eggs of crop-damaging insects consisting essentially in applying to the habitat of said eggs an ovicidal amount of a compound of the formula

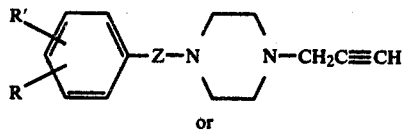

or

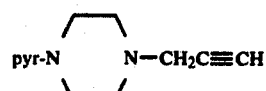

wherein "pyr" stands for 2-, 3-, or 4-pyridyl; Z is CO or $(CH_2)_n$; n is 0, 1 or 2; R is hydrogen, halogen, loweralkyl loweralkyloxy, nitro, or hydroxymethyl; and R' is hydrogen or halogen, and simple acid addition salts thereof, together with an agriculturally acceptable carrier.

2. The method of claim 1 wherein said ovicidal compound is present in said carrier at a concentration of 0.025–0.25% by weight.

3. The method of claim 1 wherein R is chlorine, R' is hydrogen and Z is $CH_2$.

4. The method of claim 3 wherein said chlorine is in the 4-position.

5. The method of claim 3 wherein said chlorine is in the 3- position.

6. The method of claim 2 wherein said compound is N'-(2-pyridyl)-N-propynylpiperazine.

7. The method of claim 2 wherein R and R' are H and Z is a single bond.

8. The method of claim 2 wherein R and R' are H and Z is $CH_2$.

9. The method of claim 2 wherein R and R' are H and Z is $-(CH_2)_2-$.